(12) United States Patent
Elliott et al.

(10) Patent No.: US 8,648,596 B2
(45) Date of Patent: Feb. 11, 2014

(54) METHOD OF AND APPARATUS FOR ANALYSIS OF THE COMPOSITION OF A SAMPLE BY ELECTRON SPIN RESONANCE (ESR) SPECTROMETRY EMPLOYING CARRIER SUPPRESSION

(75) Inventors: Colin T. Elliott, San Francisco, CA (US); Christopher John White, Portola Valley, CA (US); James R. White, San Mateo, CA (US)

(73) Assignee: Active Spectrum, Inc., Foster City, CA (US)

( * ) Notice: Subject to any disclaimer, the term of this patent is extended or adjusted under 35 U.S.C. 154(b) by 600 days.

(21) Appl. No.: 12/906,822

(22) Filed: Oct. 18, 2010

(65) Prior Publication Data

US 2011/0025328 A1    Feb. 3, 2011

Related U.S. Application Data

(63) Continuation-in-part of application No. 11/983,393, filed on Nov. 8, 2007, now Pat. No. 7,868,616, which is a continuation-in-part of application No. 11/590,522, filed on Oct. 31, 2006, now Pat. No. 7,589,529.

(51) Int. Cl.
*G01V 3/00* (2006.01)
(52) U.S. Cl.
USPC ............................................ 324/316; 324/318
(58) Field of Classification Search
USPC ........................................ 324/316, 318, 322
See application file for complete search history.

(56) References Cited

U.S. PATENT DOCUMENTS

| 3,140,993 | A | | 7/1964 | Roberts |
| 3,798,532 | A | * | 3/1974 | Hausser ......................... 324/316 |
| 4,360,776 | A | | 11/1982 | Bauman |
| 4,593,248 | A | | 6/1986 | Hyde et al. |
| 4,782,296 | A | * | 11/1988 | Schmalbein et al. ......... 324/316 |
| 4,803,624 | A | * | 2/1989 | Pilbrow et al. ................ 324/316 |
| 4,888,554 | A | * | 12/1989 | Hyde et al. .................... 324/316 |

(Continued)

FOREIGN PATENT DOCUMENTS

| DE | 198 34 939 | 2/2000 |
| JP | 2002 062271 | 2/2002 |

OTHER PUBLICATIONS

PCT International Search Report and the Written Opinion of the International Searching Authority for PCT/IB2006/003174.

(Continued)

*Primary Examiner* — Louis Arana
(74) *Attorney, Agent, or Firm* — Tope-McKay & Associates (57) ABSTRACT

Described is an electron spin resonance (ESR) spectrometer comprising a miniaturized radio-frequency (RF) microwave cavity resonator. The miniaturized RF microwave cavity resonator receives a carrier signal from a circulator, modulates the signal path signal, and reflects the carrier signal back to the circulator to amplify the carrier signal prior to demodulation. A mixer receives and demodulates the carrier signal and outputs an audio signal to generate an ESR spectrum for analyzing a chemical composition of a fluid sample. The ESR spectrum represents a magnetic susceptibility of the fluid sample to a magnetic resonance cause variation in a resonant frequency of the miniaturized RF microwave cavity resonator. In a desired aspect, the carrier signal is split into two paths prior to demodulation. The two paths are demodulated by different mixers to produce two separate outputs, an absorption spectrum and a dispersion spectrum.

19 Claims, 6 Drawing Sheets

(56) References Cited

U.S. PATENT DOCUMENTS

| | | |
|---|---|---|
| 5,233,303 A | 8/1993 | Bales et al. |
| 7,260,930 B2 | 8/2007 | Decou et al. |
| 2003/0155916 A1 | 8/2003 | Maier et al. |
| 2007/0024289 A1 | 2/2007 | Knitt et al. |

OTHER PUBLICATIONS

Chzhan, M., et al., "A Tunable Reentrant Resonator with Transverse Orientation of Electric Field forin VivoEPR Spectroscopy," Journal of Magnetic Resonance, Academic Press, Orlado, FL, US, vol. 137, No. 2, Apr. 1, 1999, pp. 373-378.

White, J., "Micro-ESR for Airborne Soot Measurement," 2008 Diesel Engine-Efficiency and Emissions Research (DEER) Conference Presentations, [online] Aug. 4, 2008, Dearborn, Michigan, Retrieved from the Internet: http://www1.eere.energy.gov/vehiclesandfuels/resources/proceedings/2008_deer_presentations.html [retrieved Nov. 25, 2008].

J. R. White, et al., "Octave-Tunable Miniature RF Resonators," IEEE Microwave and Wireless Components Letters, Vo. 15, No. 11, Nov. 2005.

\* cited by examiner

METHOD OF AND APPARATUS FOR ANALYSIS OF THE COMPOSITION OF A SAMPLE BY ELECTRON SPIN RESONANCE (ESR) SPECTROMETRY EMPLOYING CARRIER SUPPRESSION

PRIORITY CLAIM

This application is a Continuation-in-Part application of U.S. Non-Provisional application Ser. No. 11/983,393 filed on Nov. 8, 2007, entitled, "Method of and Apparatus for In-Situ Measurement of Changes in Fluid Composition by Electron Spin Resonance (ESR) Spectrometry", which is a Continuation-in-Part application of U.S. Non-Provisional application Ser. No. 11/590,522, filed on Oct. 31, 2006, entitled, "Method of and Apparatus for In-Situ Measurement of Degradation of Automotive Fluids and the Like by Micro-Electron Spin Resonance (ESR) Spectrometry", now issued as U.S. Pat. No. 7,589,529.

GOVERNMENT LICENSE RIGHTS

This invention was made with government support under Contract No. N00024-10-C-4105 awarded by the Naval Sea Systems Command of the U.S. Navy. The government has certain rights in the invention.

BACKGROUND OF THE INVENTION (1) Field of Invention

The present invention relates to the field of electron spin resonance (ESR) spectrometry and, more particularly, to the use of such technology to enable quantitative analysis of free radicals in a chemical species using a redesigned radio-frequency (RF) circuit architecture which results in a larger audio signal and, therefore, a more sensitive ESR spectrum.

(2) Description of Related Art

The monitoring of fluids in machinery, such as vehicles, engines, pumps, and the like, is essential to ensuring reliable operation of the machinery. Numerous systems have been developed by auto manufacturers and others for improved fluids management. Researchers have prototyped the use of viscosity sensors, dielectric sensors, chromatic sensors, oil pH sensors, miniature Fourier transform infrared spectrometers (FTIR) and x-ray fluorescence sensors, sensors of magnetic particles as of iron-derived and transition metal particles, and combinations thereof.

In this and related applications, microwave-frequency electron spin resonance (ESR) miniaturized spectrometers are disclosed for such direct sensing of such molecular changes resulting from the lubricant breakdown during vehicle usage. ESR spectroscopy is a technique for studying chemical species that have one or more unpaired electrons, such as organic and inorganic free radicals or inorganic complexes possessing a transition metal ion.

The ESR microwave system structures of the present invention, unlike the prior art, directly measure free radicals in the fluid passed through a sensor using a re-designed reflection-type radio-frequency circuit architecture employing a technique called carrier suppression. The ESR spectrometer described herein can perform the same chemical analysis as its larger counterparts; however, its tiny form factor and low cost open it up to countless new applications.

SUMMARY OF THE INVENTION

The present invention relates to an electron spin resonance (ESR) spectrometer for analyzing the composition of a sample. The ESR spectrometer comprises a radio frequency (RF) or a microwave source for generating a carrier signal. A power splitter splits the carrier signal into a reference path signal and a signal path signal. A circulator then receives the signal path signal and passes it to a miniaturized RF microwave cavity resonator, wherein the miniaturized RF microwave cavity resonator also receives a sample for analysis of a composition of the sample. The signal path signal is modulated and reflected back from the circulator to amplify the signal path signal prior to demodulation.

In another aspect, a mixer receives and demodulates the signal path signal and outputs an audio signal to generate an ESR spectrum for analyzing the composition of the fluid sample. The ESR spectrum represents a magnetic susceptibility of the fluid sample causing a variation in a resonant frequency of and a reflected signal amplitude from the miniaturized RF microwave cavity resonator.

In another aspect, a first mixer and a second mixer receive the reference path signal and the signal path signal as inputs, respectively, and output a first audio signal and a second audio signal.

In another aspect, an amplitude of the first audio signal contains an absorption spectrum and an amplitude of the second audio signal contains a dispersion spectrum.

In another aspect, the signal path signal reflected from the miniaturized RF microwave cavity resonator detects an audio modulation at a frequency that is the same frequency as a modulation coil around the miniaturized RF microwave cavity resonator.

In another aspect, the reference path signal and the signal path signal are split by a first 90° hybrid coupler and a second 90° hybrid coupler, respectively, prior to being received by the first mixer and the second mixer.

In another aspect, the second 90° hybrid coupler comprises an additional ninety degrees of phase length to allow the first mixer and the second mixer to generate different outputs.

In another aspect, an algorithm is employed to automatically lock a voltage controlled oscillator (VCO) to the miniaturized RF microwave cavity resonator.

In another aspect, a VCO control switch allows a tuning port of the VCO to be controlled by a digital-to-analog converter (DAC) or a phase detector integrator.

In another aspect, when a phase difference between the signal path signal and the reference path signal is at an optimal value, the phase detector integrator will lock the VCO to the miniaturized RF microwave cavity resonator.

As can be appreciated by one in the art, the present invention also comprises a method for performing the acts described herein.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to the field of electron spin resonance (ESR) spectrometry and, more particularly, to the use of such technology to enable quantitative analysis of free radicals in a chemical species using a redesigned radio-frequency (RF) circuit architecture which results in a larger audio signal and, therefore, a more sensitive ESR spectrum. The following description is presented to enable one of ordinary skill in the art to make and use the invention and to incorporate it in the context of particular applications. Various modifications, as well as a variety of uses, in different applications will be readily apparent to those skilled in the art, and the general principles defined herein may be applied to a wide range of embodiments. Thus, the present invention is not intended to be limited to the embodiments presented, but is to be accorded with the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter-clockwise have been used for convenience purposes only and are not intended to imply any particular fixed direction. Instead, they are used to reflect relative locations and/or directions between various portions of an object. As such, as the present invention is changed, the above labels may change their orientation.

(1) Specific Details

The present invention describes a scientific instrument which enables quantitative analysis of free radicals in a chemical species. A chemical species is loaded into a sensor, or ESR spectrometer, through a sample tube. As can be appreciated by one skilled in the art, the sample may be a solid of a fluid. The species can then be analyzed by the sensor to produce an ESR spectrum. The signals generated by the spectrometer can give very specific information about the molecular composition of the species that otherwise might be difficult or impossible to determine. The present invention can be employed as a general purpose laboratory instrument, or tailored to fit a specific application including on-line chemical analysis.

Applications for the present invention include, but are not limited to, an affordable, general-purpose bench-top ESR spectrometer for industry, science, or education; an on-line or in-line sensor for lubricants and hydraulic fluids, allowing real-time analysis of critical chemical properties; oxidation and shelf-life studies for food and drink products; and industry-specific applications, such as for petroleum analysis and as a biomedical research tool.

The invention described herein features a re-designed RF circuit architecture at the heart of the ESR spectrometer. U.S. patent application Ser. No. 11/983,393 entitled, "Method of and Apparatus for In-Situ Measurement of Changes in Fluid Composition by Electron Spin Resonance (ESR) Spectrometry" (hereinafter referred to as the '393 application) described a sensor employing a transmission-type design, in which the RF carrier signal would be transmitted through a two-port resonator. The '393 application is hereby incorporated by reference as though fully set forth herein. As disclosed in the '393 application, as the RF carrier signal passed through the spectrometer, the carrier would pick up an audio-frequency modulation signal which would change if there were unpaired electrons reacting to the particular magnetic field and resonator frequency combination. This signal was then demodulated through a mixer and amplified to produce an ESR spectrum.

In contrast, the present invention uses a reflection-type design to employ a technique called carrier suppression. In this architecture, the RF carrier is passed through a circulator into a resonator (a non-limiting example of which includes a one-port resonator), which then reflects the modulated signal. When the resonator is critically coupled, the reflected RF signal power is much lower than the incident RF power, for example, by −16 dB or more, as shown as a non-limiting example in FIG. 5. Thus, the resulting RF carrier signal is much smaller than in the transmission design of the '393 application. However, the modulation sideband power on the reflected signal is substantially the same as for the transmission design. This allows the modulated carrier to be greatly amplified before demodulating with a mixer, resulting in a larger audio signal and, therefore, a more sensitive ESR spectrum. Further, because the RF carrier phase noise can be a limiting factor in the spectrometer sensitivity, the reflection design increases the signal-to-noise between the RF signal phase-noise and the desired modulation sidebands containing the ESR spectrum information.

In a desired aspect, the carrier signal is split into two paths before being demodulated, one of which has an additional ninety degrees of phase length. These two paths are then demodulated by different mixers to produce two separate outputs, an absorption spectrum and a dispersion spectrum. Together, these two signals generate more ESR information than either one by itself.

Figure 1:
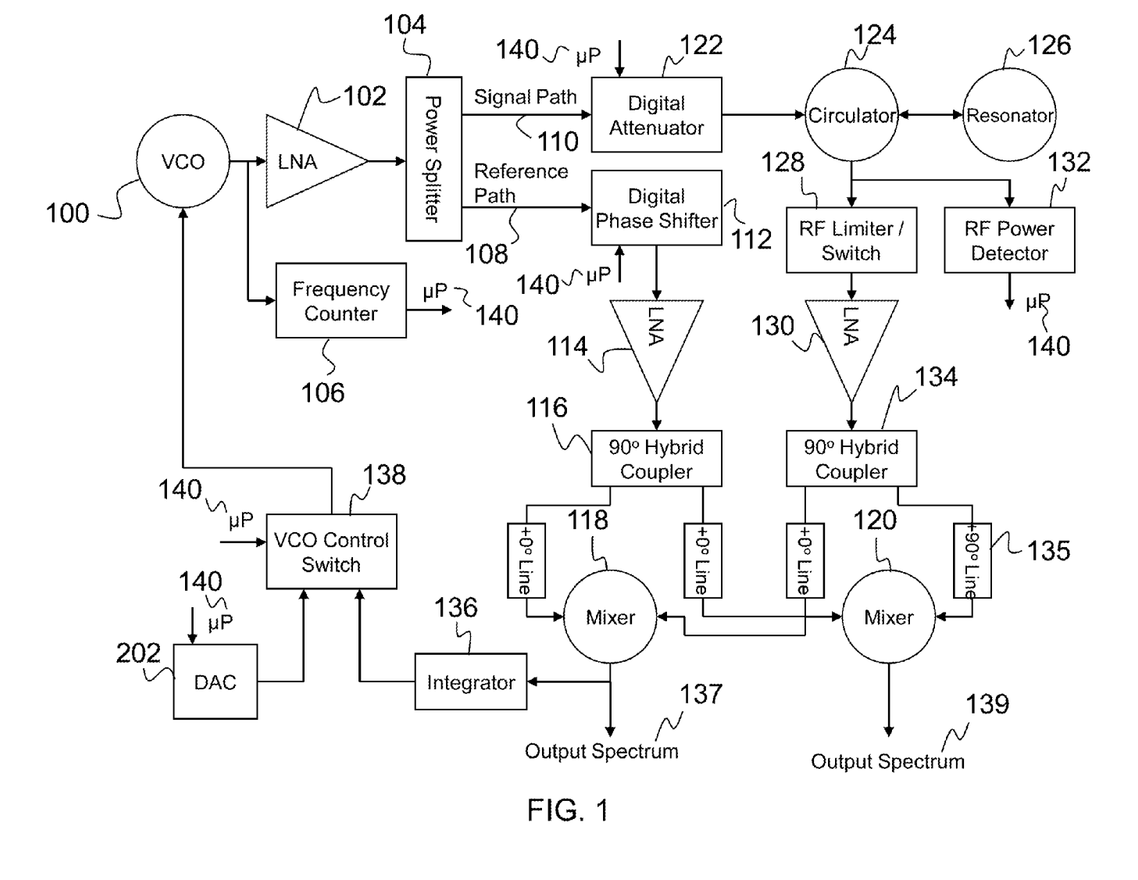
FIG. 1 is a block diagram depicting the RF circuitry of an ESR spectrometer according to the present invention.

FIG. 1 shows a block diagram of the RF circuitry of the electron spin resonance spectrometer according to the present invention. A radio frequency or microwave source generates a carrier signal (i.e., RF signal). As a non-limiting example, a voltage controlled oscillator (VCO) 100 generates a RF signal which is amplified by a first low noise amplifier (LNA) 102. As can be appreciated by one skilled in the art, several types of VCOs may be used. Non-limiting examples of VCOs include a low-phase noise, low-vibration sensitivity, surface mounted VCO, such as model CRO3170C-LF from Z-Communications, Inc. (San Diego, Calif.) and model DCRO307331-10 from Synergy Microwave Corporation (Paterson, N.J.). Another non-limiting example of a VCO, such as model CRO3170C-LF, is a coaxial resonator based oscillator with a tuning range of 3070-3270 MHz and a phase noise of −108 dBc/Hz @ 10 kHz offset, according to the manufacturer specifications. Additionally, VCO model DCRO307331-10 is based on use of stripline resonators, which may have reduced vibration sensitivity compared to coaxial resonators, and is tunable from 3075 to 3310 MHz. The phase noise specification for model DCRO307331-10 is −100 dBc/Hz @ 10 kHz offset.

The LNA 102 additionally provides isolation between the VCO 100 and reflections from a power splitter 104. A small part of the RF signal is tapped off to be measured by a frequency counter 106. The remaining power is split by the power splitter 104 into two channels: a reference path 108 and a signal path 110. The reference path 108 passes through a digitally-controlled phase shifter 112 and into a second LNA 114. This signal is then split by a 90° hybrid coupler 116 and drives the local oscillator (LO) inputs of mixers 118 and 120. The signal path 110 goes through a digitally-controlled attenuator 122 and into a circulator 124, which passes the RF power through to a resonator 126.

When the VCO 100 is correctly locked to the cavity resonance, most of the power is absorbed and a much smaller signal is reflected back to the circulator 124. This reflected RF carrier signal will pick up an audio modulation at the same frequency as a modulation coil around the resonator 126. The signal is passed by the circulator 124 to a different path consisting of a RF limiter (or switch) 128 and a third LNA 130. The RF limiter/switch 128 will prevent the LNA 130 from being damaged if too much power is reflected. A small portion of the power is also tapped off and measured with a RF power detector 132. Relative changes in the RF power at the resonator output indicate changes in the resonator loss, for example, due to dielectric loss in the fluid sample. As a non-limiting example, the present invention uses low-cost RF power detectors, such as model LTC5508 from Linear Technology, Inc. (Milpitas, Calif.). The amplified signal is again divided into two even parts by another 90° hybrid coupler 134, which drive the RF inputs of mixers 118 and 120. One section has an additional ninety degrees of phase 135 which allows the two mixers to generate different outputs.

The reference signal demodulates the carrier from the signal path 110, and the mixers 118 and 120 each output an audio signal. A first output spectrum 137 (i.e., absorption) is synchronously demodulated from a first audio signal, while a second output spectrum 139 (i.e., dispersion spectrum) is synchronously demodulated from a second audio signal. The amplitude of the first audio signal contains the absorption spectrum, and the amplitude of the second audio signal contains the dispersion spectrum. An ESR spectrum for analyzing the composition of the sample is generated, wherein the ESR spectrum represents a magnetic susceptibility of the sample causing a variation in the resonant frequency of and reflected signal from the miniaturized RF microwave cavity resonator.

One mixer 118 may also be used as a phase detector to lock the VCO 100. The direct current (DC) output is passed through an integrator 136 and back into the VCO tuning input (VCO control switch 138). When the phase shifter 112 is set to the correct value, the VCO 100 will lock to the resonant frequency of the cavity. In FIG. 1, μP denotes microprocessor 140, and the arrows represent inputs and outputs to and from the microprocessor, which will be described below.

Figure 2:
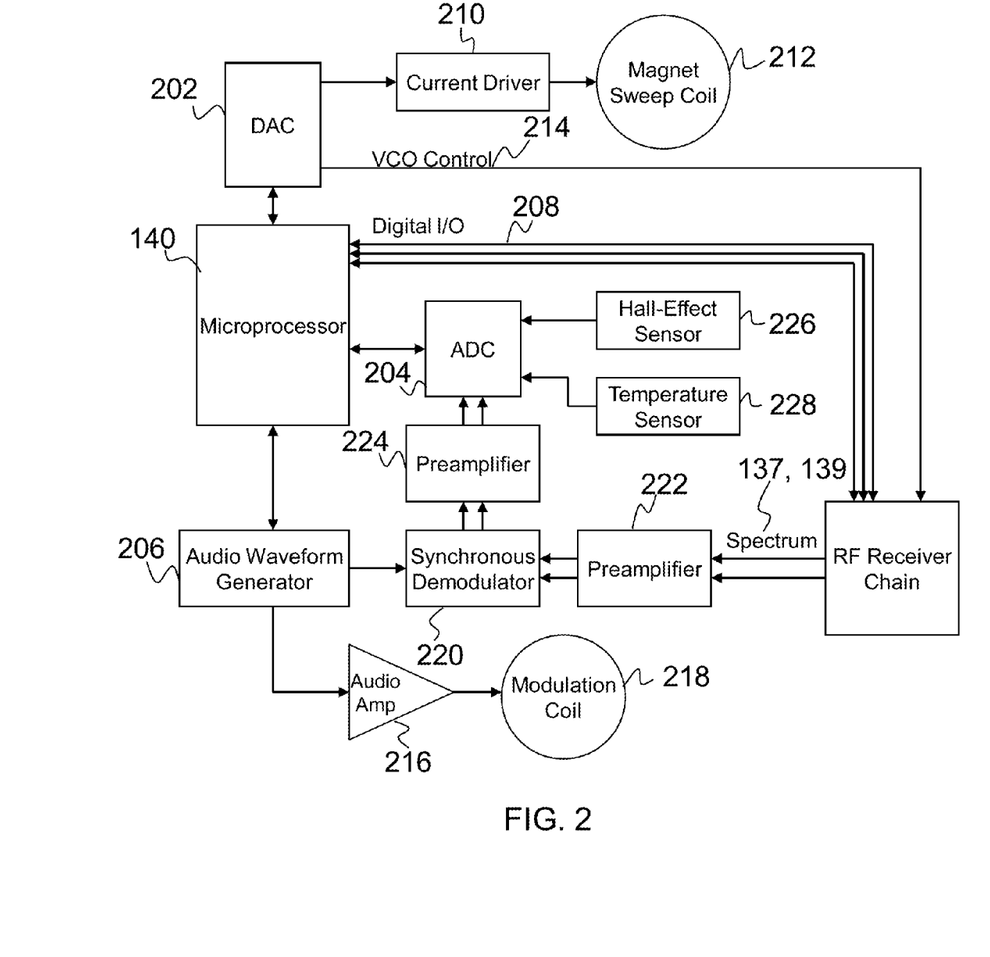
FIG. 2 is a block diagram depicting the audio-frequency and digital components of the ESR spectrometer according to the present invention.

The audio-frequency and digital components of the spectrometer are shown in FIG. 2. A microprocessor 140 controls a digital-to-analog converter (DAC) 202, an analog-to-digital converter (ADC) 204, an audio waveform generator 206, and many input/output (I/O) channels 208. The DAC 202 controls a current driver 210 which drives a magnet sweep coil 212, and also allows direct control of the VCO (VCO control 214). The audio waveform generator 206 produces an audio-frequency sine wave that goes through an audio amplifier (amp) 216 to a modulation coil 218 around the resonator (FIG. 1, 126), as well as a square wave that is used to drive a synchronous demodulator 220. The two audio signals that come out of the mixers (FIGS. 1, 118 and 120) are amplified with a first preamplifier 222, demodulated by the synchronous demodulator 220, amplified again by a second preamplifier 224, and read by the ADC 204. The ADC 204 also reads values from a hall-effect sensor 226 and a temperature sensor 228.

Referring to FIG. 1, an algorithm is employed to automatically lock the VCO 100 to the resonator 126. The VCO control switch 138 allows a tuning port of the VCO 100 to be either controlled directly by a DAC 202, or to be controlled by the phase detector integrator 136 of the RF receiver chain. First the microprocessor 140 sets the VCO control switch 138 to DAC 202 control and sweeps the full voltage range of the VCO 100. During this sweep, the microprocessor 140 measures the frequency counter 106 and output power being reflected from the resonator 126 with an RF power detector 132. At resonant frequency, the resonator 126 cavity will absorb the maximum amount of power, and the reading from the RF power detector 132 will be at a minimum. The microprocessor 140 then sets the VCO control switch 138 to phase detector integrator 136 control. When the phase difference between the signal path 110 and the reference path 108 shown in FIG. 1 is at an optimal value, the phase detector integrator 136 will correctly lock the VCO 100 to the resonator 126. To find this, the microprocessor 140 steps the digital phase shifter 112 in the reference path 108 through a full 360 degrees. After each step, the frequency and output power are recorded. The microprocessor 140 looks in this data set to find the phase settings which most closely match the frequency and power conditions that it determined to be correct during the VCO sweep. It then sets the phase detector integrator 136 to these settings, and the system is optimally locked.

Figure 3:
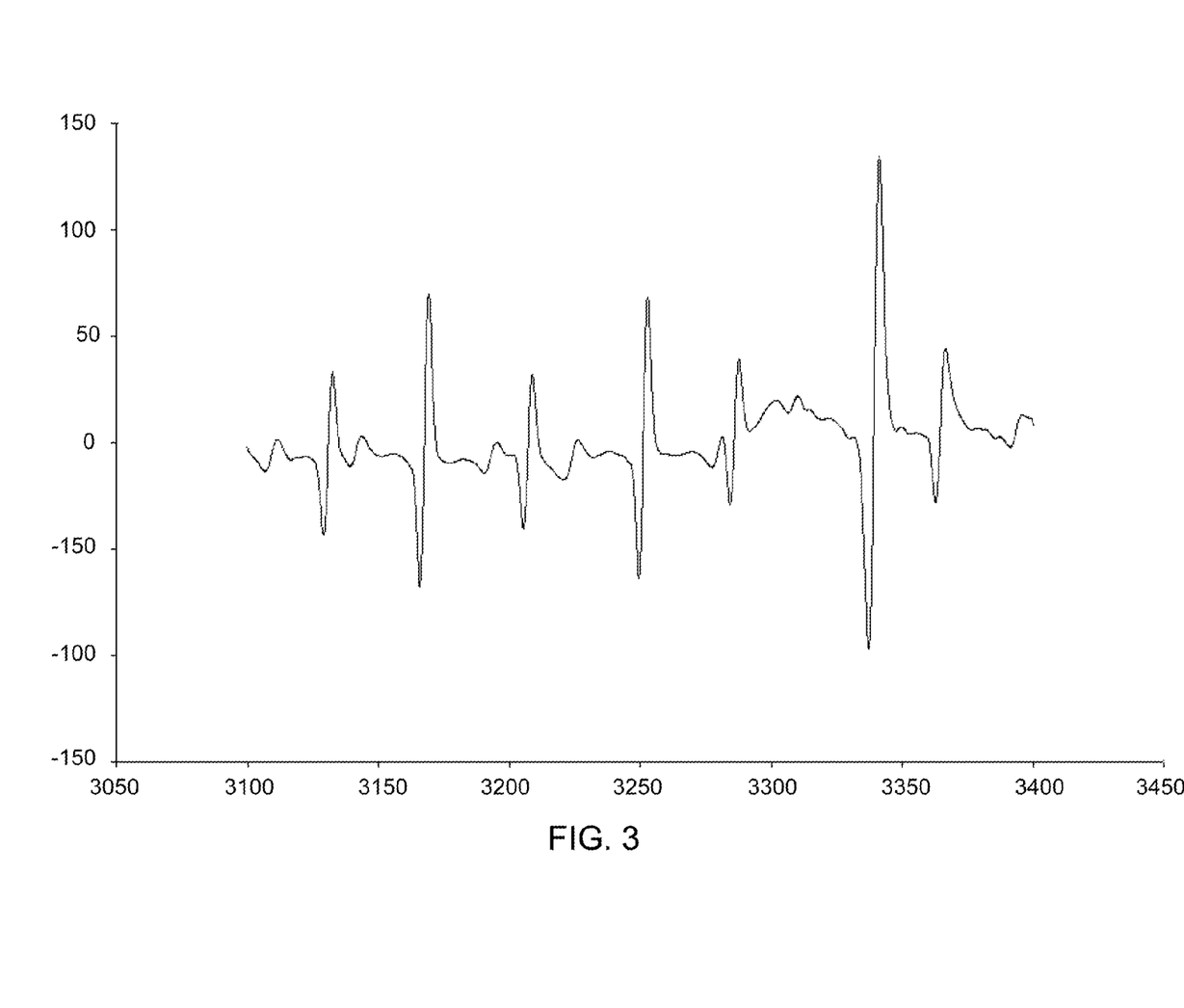
FIG. 3 illustrates an ESR absorption spectrum from analyzing shards of vanadium-doped magnesium oxide crystal according to the present invention.

FIG. 3 shows an ESR derivative of an absorption spectrum from analyzing shards of vanadium-doped magnesium oxide crystal. The x-axis is magnetic field (Gauss), and the y-axis is relative intensity of the output. The spikes on the spectrum correspond to free electrons which resonate at specific magnetic field strengths. The intensity is unitless, but can be quantitatively associated with electron spin density through controlled experiments.

Figure 4:
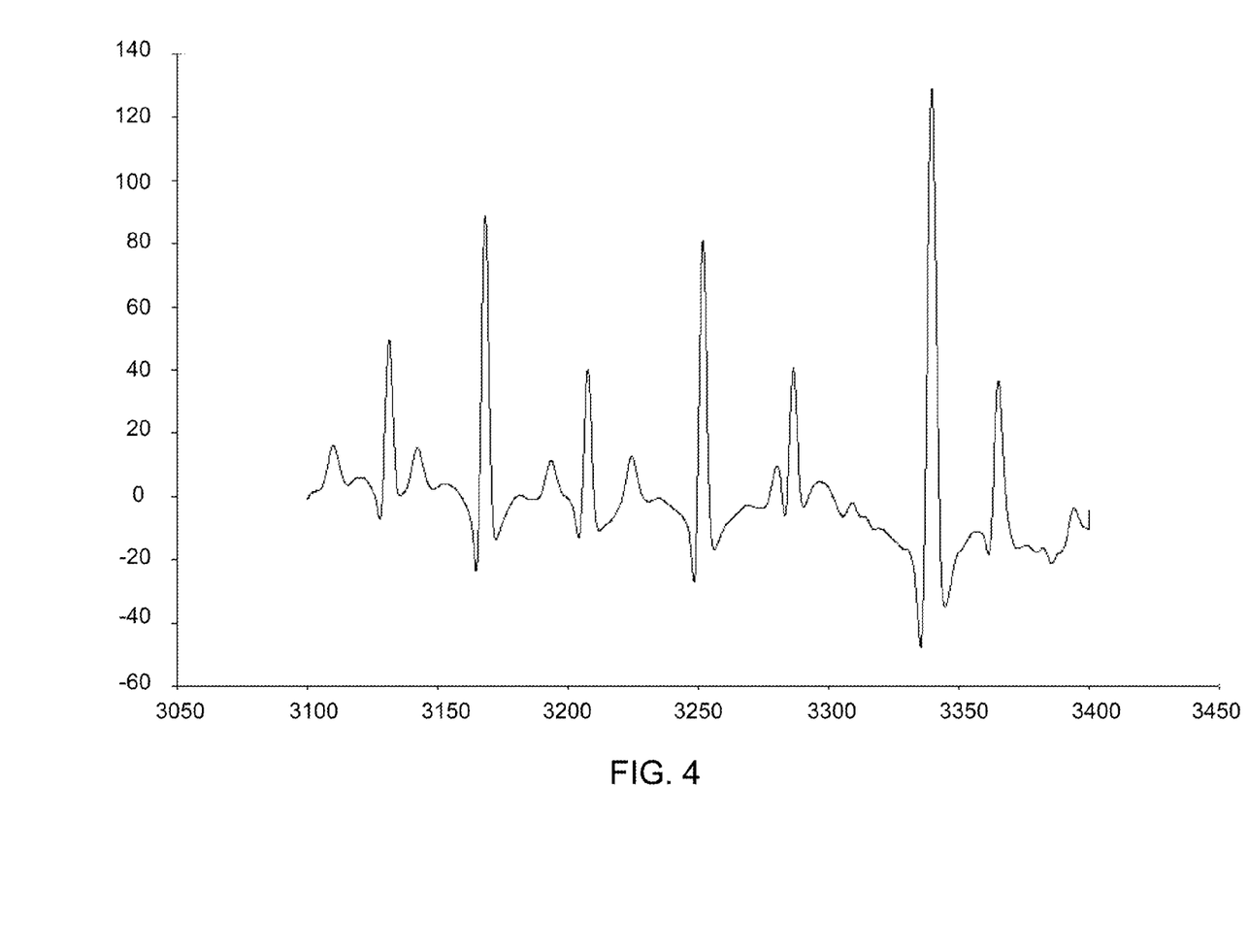
FIG. 4 illustrates an ESR dispersion spectrum from analyzing shards of vanadium-doped magnesium oxide crystal according to the present invention.

FIG. 4 shows an ESR derivative of a dispersion spectrum from the same crystal that was used to generate the results depicted in FIG. 3. The absorption and dispersion components of the spectrum are mathematically related through the Kramers-Kronig relation.

Figure 5:
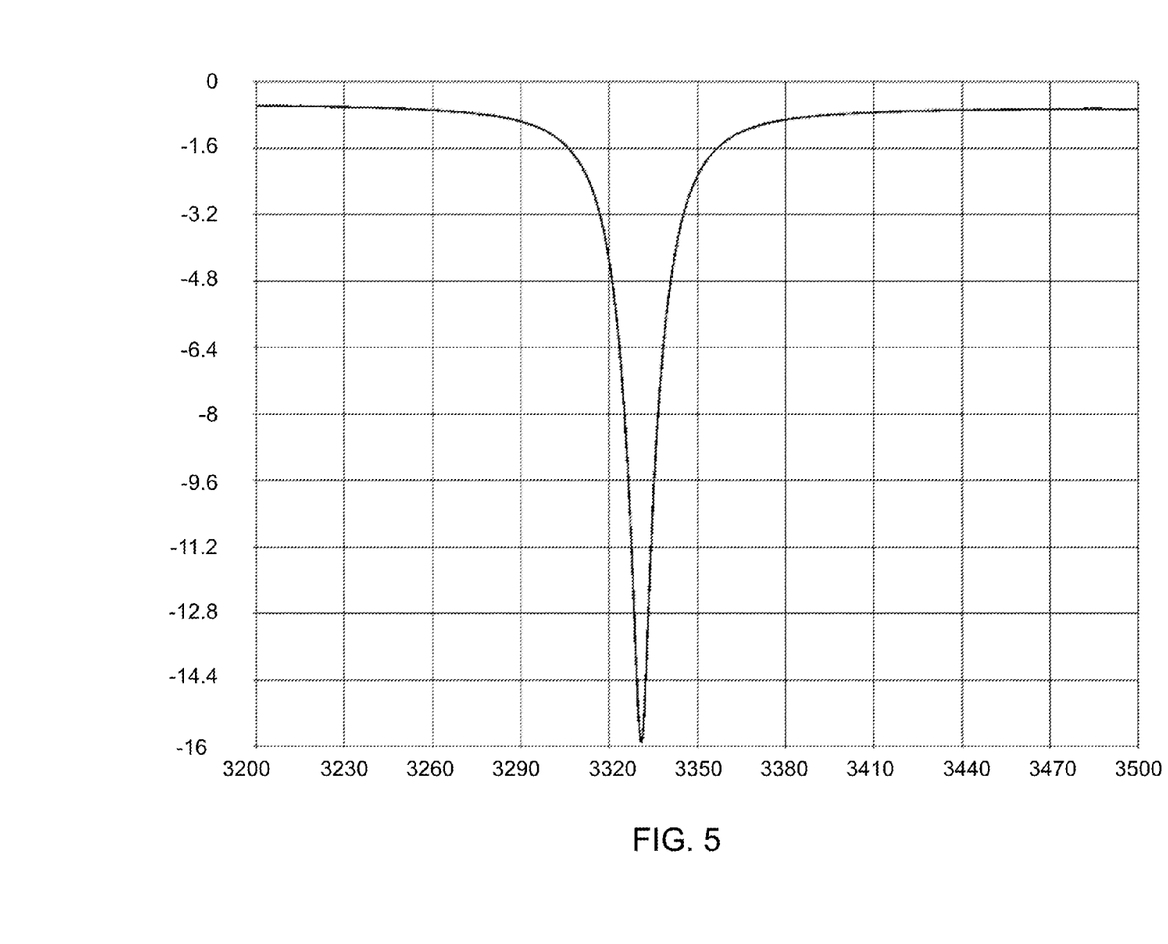
FIG. 5 illustrates the S11 magnitude of a miniature resonator taken with a vector network analyzer according to the present invention.

FIG. 5 is the S11 magnitude of a miniature resonator taken with a vector network analyzer. This example has a resonance of 3335 MHz. When a VCO-generated carrier signal is driven into the resonator at this frequency, the reflected signal is suppressed.

Figure 6:
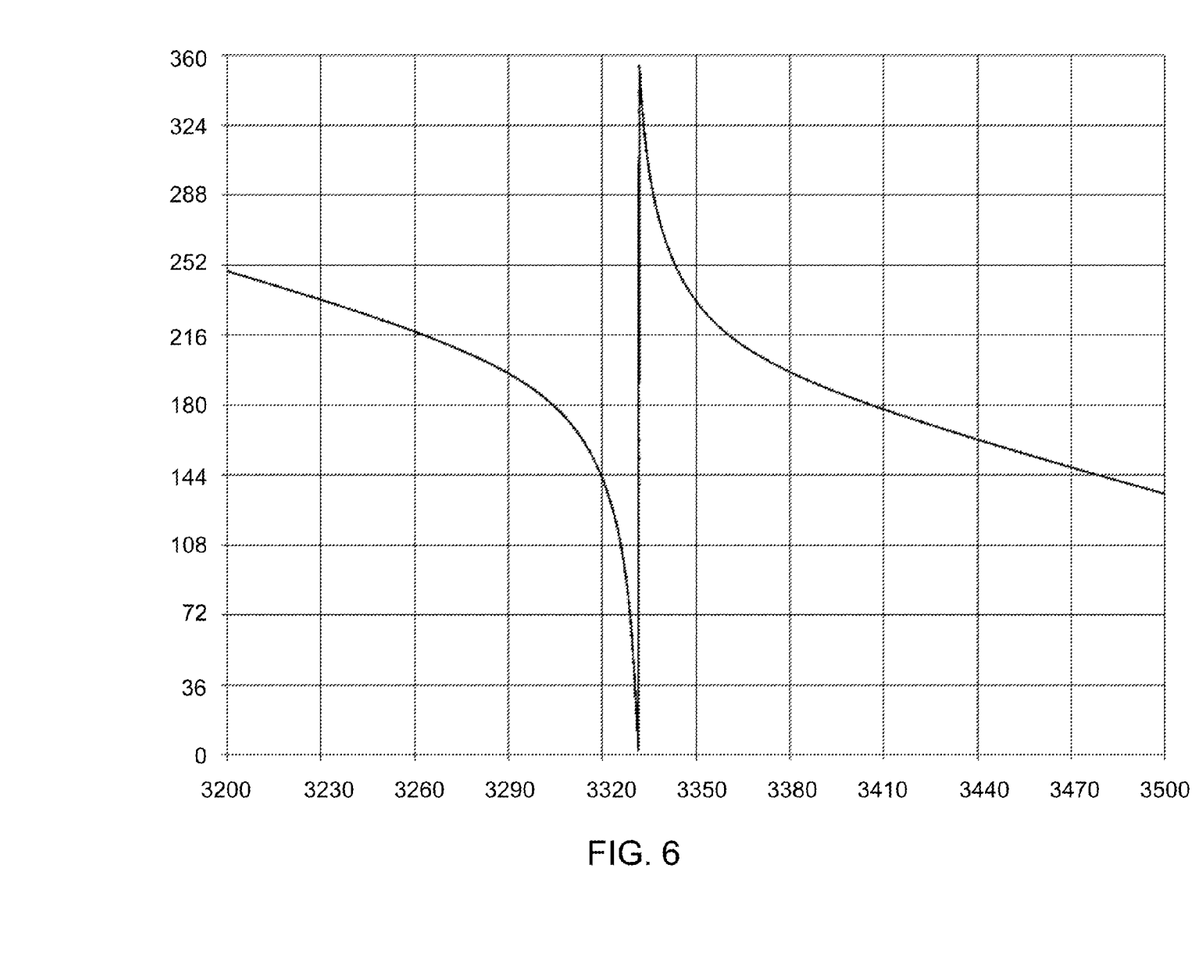
FIG. 6 illustrates the S11 phase response of a miniature resonator taken with a vector network analyzer according to the present invention.

FIG. 6 is the S11 phase response of the same miniature resonator that was used to generate the results depicted in FIG. 5. This signal can be extracted from the carrier by demodulating through a mixer, and the resulting DC output is used to lock the VCO to the resonator through an integrator feedback loop.

What is claimed is:

1. An electron spin resonance (ESR) spectrometer for analyzing the composition of a sample comprising:
   a radio frequency (RF) or microwave source for generating a carrier signal;
   a power splitter for splitting the carrier signal into a reference path signal and a signal path signal;
   a circulator for receiving the signal path signal and a digital phase shifter for receiving the reference path signal;
   a miniaturized RF microwave cavity resonator, wherein the miniaturized RF microwave cavity resonator receives the signal path signal from the circulator, modulates the signal path signal, and reflects the signal path signal back from the circulator to amplify the signal path signal prior to demodulation; and
   a pair of mixers, wherein a first mixer demodulates the signal path signal and a second mixer demodulates the reference path signal to produce an absorption spectrum and a dispersion spectrum which are used to generate an ESR spectrum for analyzing the composition of a sample received by the miniaturized RF microwave cavity resonator;
   wherein the ESR spectrum represents a magnetic susceptibility of the sample causing a variation in a resonant frequency of and reflected signal from the miniaturized RF microwave cavity resonator.

2. The ESR spectrometer as set forth in claim 1, further comprising a mixer for receiving and demodulating the signal path signal and outputting an audio signal to generate an ESR spectrum for analyzing the composition of the sample, wherein the ESR spectrum represents a magnetic susceptibility of the sample causing a variation in a resonant frequency of and a reflected signal amplitude from the miniaturized RF microwave cavity resonator.

3. The ESR spectrometer as set forth in claim 2, further comprising a first mixer and a second mixer for receiving the reference path signal and the signal path signal as inputs, respectively, and outputting a first audio signal and a second audio signal.

4. The ESR spectrometer as set forth in claim 3, wherein an amplitude of the first audio signal contains an absorption spectrum and an amplitude of the second audio signal contains a dispersion spectrum.

5. The ESR spectrometer as set forth in claim 4, wherein the signal path signal reflected from the miniaturized RF microwave cavity resonator detects an audio modulation at a frequency that is the same frequency as a modulation coil around the miniaturized RF microwave cavity resonator.

6. The ESR spectrometer as set forth in claim 5, wherein the reference path signal and the signal path signal are split by a first 90° hybrid coupler and a second 90° hybrid coupler, respectively, prior to being received by the first mixer and the second mixer.

7. The ESR spectrometer as set forth in claim 6, wherein the second 90° hybrid coupler comprises an additional ninety degrees of phase length to allow the first mixer and the second mixer to generate different outputs.

8. The ESR spectrometer as set forth in claim 7, wherein an algorithm is employed to automatically lock a voltage controlled oscillator (VCO) to the miniaturized RF microwave cavity resonator.

9. The ESR spectrometer as set forth in claim 8, wherein a VCO control switch allows a tuning port of the VCO to be controlled by a digital-to-analog converter (DAC) or a phase detector integrator.

10. The ESR spectrometer as set forth in claim 9, wherein when a phase difference between the signal path signal and the reference path signal is at an optimal value, the phase detector integrator will lock the VCO to the miniaturized RF microwave cavity resonator.

11. A method of using electron spin resonance (ESR) spectrometry Liar analyzing the composition of a sample, comprising acts of:
   generating a carrier signal;
   splitting the carrier signal with a power splitter, wherein the carrier signal is split into a reference path signal and a signal path signal;
   receiving of the signal path signal by a circulator and the reference path signal by a digital phase shifter;
   receiving of a sample by a miniaturized RF microwave cavity resonator;
   receiving the signal path signal from the circulator by the miniaturized RF microwave cavity resonator;
   modulating the signal path signal;
   reflecting the signal path signal back from the circulator to amplify the signal path signal prior to demodulation; and
   demodulating the signal path signal and the reference path signal by a pair of mixers to produce an absorption spectrum and a dispersion spectrum which are used to generate an ESR spectrum for analyzing the composition of the sample;
   wherein the ESR spectrum represents a magnetic susceptibility of the sample causing a variation in a resonant frequency of and reflected signal from the miniaturized RF microwave cavity resonator.

12. The method of using ESR spectrometry as set forth in claim 11, further comprising acts of:
   receiving and demodulating of the signal path signal by a mixer; and
   outputting an audio signal to generate an ESR spectrum for analyzing the composition of the sample, wherein the ESR spectrum represents a magnetic susceptibility of the sample causing a variation in a resonant frequency of and a reflected signal amplitude from the miniaturized RF microwave cavity resonator.

13. The method of using ESR spectrometry as set forth in claim 12, further comprising acts of:
   receiving the reference path signal as an input by a first mixer;
   receiving the signal path signal as an input by a second mixer; and
   outputting a first audio signal and a second audio signal.

14. The method of using ESR spectrometry as set forth in claim 13, further comprising acts of:
   synchronously demodulating an absorption spectrum from the first audio signal; and
   synchronously demodulating a dispersion spectrum from the second audio signal.

15. The method of using ESR spectrometry as set forth in claim 14, wherein the signal path signal reflected from the miniaturized RF microwave cavity resonator detects an audio modulation at a frequency that is the same frequency as a modulation coil around the miniaturized RF microwave cavity resonator.

16. The method of using ESR spectrometry as set forth in claim 15, further comprising an act, of splitting of the reference path signal and the signal path signal by a first 90° hybrid coupler and a second 90° hybrid coupler, respectively, prior to being received by the first mixer and the second mixer.

17. The method of using ESR spectrometry as set forth in claim 16, further comprising an act of employing an algorithm to automatically lock a voltage controlled oscillator (VCO) to the miniaturized RF microwave cavity resonator.

18. The method of using ESR spectrometry as set forth in claim 17, further comprising an act of using a VCO control switch to allow a tuning port of the VCO to be controlled either by a digital-to-analog converter (DAC) or a phase detector integrator.

19. The method of using ESR spectrometry as set forth in claim 18, further comprising an act of using, the phase detector integrator to lock the VCO to the miniaturized RF microwave cavity resonator when a phase difference between the signal path signal and the reference path signal is at an optimal value.

* * * * *